United States Patent
Jones et al.

(10) Patent No.: US 9,534,166 B2
(45) Date of Patent: Jan. 3, 2017

(54) FAMILIES OF SCALE-INHIBITORS HAVING DIFFERENT ABSORPTION PROFILES AND THEIR APPLICATION IN OILFIELD

(75) Inventors: Chris Jones, Cheslyn Hay (GB); Dominique Labarre, Neuilly sur Seine (FR); Carole Rouault, Villepinte (FR); James Wilson, Coye la Foret (FR)

(73) Assignee: RHODIA OPERATIONS, Aubervilliers (FR)

( * ) Notice: Subject to any disclaimer, the term of this patent is extended or adjusted under 35 U.S.C. 154(b) by 638 days.

(21) Appl. No.: 13/980,660

(22) PCT Filed: Jan. 19, 2012

(86) PCT No.: PCT/EP2012/050781
§ 371 (c)(1),
(2), (4) Date: Sep. 27, 2013

(87) PCT Pub. No.: WO2012/098186
PCT Pub. Date: Jul. 26, 2012

(65) Prior Publication Data
US 2014/0014335 A1    Jan. 16, 2014

Related U.S. Application Data

(60) Provisional application No. 61/434,187, filed on Jan. 19, 2011.

(51) Int. Cl.
| | | |
|---|---|---|
| *E21B 37/06* | (2006.01) | |
| *C09K 8/528* | (2006.01) | |
| *C09K 8/588* | (2006.01) | |
| *E21B 43/14* | (2006.01) | |
| *C08F 12/30* | (2006.01) | |
| *C08F 212/14* | (2006.01) | |
| *C08F 228/02* | (2006.01) | |
| *C07F 9/38* | (2006.01) | |

(52) U.S. Cl.
CPC ............. *C09K 8/528* (2013.01); *C07F 9/3847* (2013.01); *C08F 12/30* (2013.01); *C08F 212/14* (2013.01); *C08F 228/02* (2013.01); *C09K 8/588* (2013.01); *E21B 37/06* (2013.01); *E21B 43/14* (2013.01)

(58) Field of Classification Search
CPC ............. C09K 8/528; C09K 8/54; C09K 8/74; E21B 37/06; E21B 43/16
See application file for complete search history.

(56) References Cited

U.S. PATENT DOCUMENTS

| | | | |
|---|---|---|---|
| 6,063,289 A | 5/2000 | Failon | |
| 6,071,434 A | 6/2000 | Davis | |
| 6,077,461 A | 6/2000 | Murray et al. | |
| 6,123,869 A | 9/2000 | Lawson | |
| 2007/0267193 A1 | 11/2007 | Hills | |

FOREIGN PATENT DOCUMENTS

| | | |
|---|---|---|
| CN | 1846040 A | 10/2006 |
| EA | 008243 B1 | 4/2007 |
| EA | 013605 B1 | 6/2010 |
| EP | 0861846 A2 | 9/1998 |
| EP | 1639228 B1 | 4/2008 |
| RU | 2256071 C2 | 7/2005 |
| WO | 0181654 A1 | 11/2001 |
| WO | WO 03029153 A2 | 4/2003 |
| WO | WO 2005/001241 A2 | 1/2005 |

OTHER PUBLICATIONS

Chinese Patent Office; Chinese Search and Exam Report for Application No. 201280005862.2 dated Mar. 17, 2015.
WIPO, International Search Report for PCT/EP2012/050781 dated Mar. 26, 2012.
Russian Patent Office; Russian Patent Application No. 2013138462; Decision to Grant dated Jan. 15, 2015; 6 pages.

*Primary Examiner* — Zakiya W Bates
(74) *Attorney, Agent, or Firm* — Christopher J. Knors; Moore & Van Allen PLLC

(57) ABSTRACT

The current invention relates to families of scale-inhibitors having different UV/VIS absorption profiles and their application in a method for stimulating an oilfield comprising those families.

15 Claims, No Drawings

FAMILIES OF SCALE-INHIBITORS HAVING DIFFERENT ABSORPTION PROFILES AND THEIR APPLICATION IN OILFIELD

CROSS-REFERENCE TO RELATED APPLICATIONS

This application is filed under the provisions of 35 U.S.C. §371 and claims the benefit of International Patent Application No. PCT/EP2012/050781, filed on Jan. 19, 2012, which claims the benefit of U.S. Provisional patent application 61/434,187, filed in the United States Patent and Trademark Office on Jan. 19, 2011; all of which are hereby incorporated by reference in their entirety.

The current invention relates to families of scale-inhibitors having different UV/VIS absorption profiles, which may be used in a method for stimulating an oilfield, especially for providing an enhanced scale inhibition during secondary oil recovery.

In oil recovery and, more importantly, in secondary oil recovery (where a fluid, preferably a water-based fluid, such as sea water, is injected into an oil well in order to displace the crude oil), inorganic deposits of scale may cause blockage of pipework and the pores in the oil-bearing strata, thus reducing or even preventing the flow of oil. Thus, the scale decreases oil recovery yields.

Current methods for inhibiting formation of inorganic deposits of scale employ compounds containing phosphorus, usually polymers of the carboxylic acid, sulfonic acid, or phosphonic type.

For example, organic phosphonic acids are described in U.S. Pat. No. 6,063,289 and U.S. Pat. No. 6,123,869. Acrylic polymers containing a phosphinate or phosphonate group can also be used, for example a copolymer of methacrylic acid with phosphate functionality for treating industrial water (U.S. Pat. No. 4,209,398). U.S. Pat. No. 6,071,434 teaches the use as scale inhibitors of polymers prepared by copolymerisation of Sodium Vinyl Sulphonate (SVS) and Acrylic acid (AA) in the presence of a transfer agent. This polymer has been developped as a scale inhibitor for squeeze treatment of oilfields. Patent WO02003/029153 describes compositions for inhibition of inorganic deposits in the petroleum sector by means of terpolymers having a phosphate monomer, methallyl hydroxy phosphate.

Treatment levels up to a few hundred parts per million (ppm) are usually effective. The scale-inhibiting polymer is typically added to the fluid to be treated or may be applied to oil bearing formations by means of "squeeze treatment". Squeeze treatment involves pumping scale inhibitor into an oil production well so that the inhibitor enters the formation rock and is retained there. When the well is put back into production, the produced fluids are treated by the scale inhibitor which leaches out of the formation rock. Thus the scale inhibitor is released in a fluid. The scale inhibitor may be applied in an aqueous or non-aqueous medium. The objective is to prevent or control the scale formation in systems wherein the fluid is used.

Scale formation is only controlled if the scale inhibitor polymer is present at a treatment level within the product's defined effective range, for example of the minimum inhibitor concentration (MIC) of the specific system (water+scale inhibitor). During production, when the inhibitor has been released, for example by consumption, there is a need for re-squeezing. With squeeze treatment, the concentration of the scale inhibitor in the produced fluids will diminish over time till a repeat "re-squeeze" operation is necessary. Also, scale inhibitor may be lost through, e.g. absorption or degradation. Hence, there is a need to replenish the scale inhibitor to replace this loss. Below the effective range of concentration of the polymer, effective scale control will not be maintained resulting in scale build up, the consequences of which is often catastrophic in this application. Overall, it can be seen that the concentration of scale inhibitor in the treated fluids is vitally important and chemical analysis of scale control polymers has always been difficult at ppm levels.

The problem of analysis has recently become more difficult in sub sea oilfields because of sub sea completions where several individual wells are communed on the seabed and the combined fluids are piped to the nearest production platform which may be several tens of miles away. In that configuration, if the oil yield decreases in the recovered combined fluid, it is not possible to determine the particular well that has too much scale, and/or to determine the well wherein scale inhibitor should be added. Because of that it is sometimes necessary to stop the production for all the wells, or to add too much scale inhibitor (for example by adding to much scale inhibitor in a well wherein less is needed). That decreases the global productivity and/or is not cost effective.

A solution to that problem of decreasing global productivity is described in EP 1639228 teaching a production method by injecting an inflow stream of a fluid into an oil producing well linked to the oilfield, displacing the oil and recovering an outflow stream of fluid comprising the oil, wherein at least two streams are injected into at least two production zones of an oil well or are injected into at least two different oil producing wells from which at least two outflow streams from the two zones or wells are combined before recovering, with a scale inhibitor having detectable moieties being introduced into the oilfield(s) and/or into the fluids, characterized in that two different scale inhibitors are used, dedicated to the two zones or wells, said different scale inhibitors having different detectable moieties that can be distinguished by analyzing. These operations are also referred to as a production method, the individual determination of at least 2 returned inhibitor concentrations allows the improved management of scale in multiple zones, opening up the possibility of squeezing the different zones independently when each inhibitor drops to a defined concentration.

Although the EP 1639228 method constitutes a great improvement per se, this method reveals, in practice, difficult to be carried out. Especially, there is a need of inhibitor polymers presenting sufficiently different spectroscopic absorption profiles.

One aim of the current invention is to provide a method for inhibiting inorganic deposits in a petroleum reservoir allowing to solve the problem of decreasing global productivity in a better way than the method generally disclosed in EP 1639228.

To this end, the instant invention proposes to make use, in a method of the type disclosed in EP 1639228, of specific scale inhibitor polymers of two distinct families which actually have different absorption profiles in UV/VIS spectroscopy. More precisely, the invention makes use of polymers having different detectable moieties by means of distinct absorption maxima, so that they can be distinguished by analyzing by means of absorption analytical methods such as UV/VIS spectroscopy.

In this scope, the invention provides two families of polymers having different absorption profiles in UV/VIS spectroscopy and having good antiscale properties, and a method for the preparation of such polymers.

More precisely, according to a first aspect, the invention relates to a method for imparting scale inhibition in an oilfield comprising the steps of:
a) injecting at least two inflow streams of a fluid into at least two production zones of an oil producing well linked to the oilfield, or into at least two different oil producing wells from which at least two outflow streams from the two zones or wells are combined, before recovering, with a scale inhibitor having detectable moieties being introduced into the oilfield(s) and/or into the fluid, wherein two different scale inhibitors are used, each dedicated to one of the two zones or wells, said different scale inhibitors having different detectable moieties thanks to their distinct absorption maxima that are distinguished by a spectroscopic absorption analytical method;
b) displacing the oil,
c) recovering an outflow stream of fluid comprising the oil,
d) measuring the amounts of the different scale inhibitors in the recovered stream of fluid by absorption analytical method, or of a fluid derived therefrom, and,
e) optionally, addressing a scale formation problem that occurs in the zone or well the scale inhibitor is dedicated to if the amount of a scale inhibitor is below a given value, wherein:
one of the two distinct scale inhibitors is a polymer (P1) as obtained by polymerization of:
an ethylenically unsaturated carboxylic monomer;
an ethylenically unsaturated sulphonic acid monomer or water soluble salts thereof;
a styrene monomer which can be substituted by one to three groups identical or different,
in the presence of an hypophosphorous adduct of the formula (A1):

$(X_2O_3P)_2CHYPO_2X_2$                                                       (A1)

wherein:
X is H or an alkali metal, alkaline earth or ammonium, preferably Na,
Y is an alkylene group linear or branched having 1 to 5 carbon atoms, preferably a methylene, or an ethylene group;
and
the other scale inhibitor is a polymer (P2) as obtained by polymerization of:
an ethylenically unsaturated carboxylic monomer;
an ethylenically unsaturated sulphonic acid monomer or water soluble salts thereof;
a vinyl heteroaromatic monomer comprising at least one heteroatom selected from N, P or O which can be substituted by at least one hydrocarbon group having 1 to 6 carbon atoms and optionally containing functional groups such as sulphate, carboxylate, phosphonate and/or phosphinate,
in the presence of an hypophosphorous adduct of the formula (A2) (which is identical to or distinct from adduct A1):

$(X_2O_3P)_2CHYPO_2X_2$                                                       (A2)

wherein:
X is H or an alkali metal, alkaline earth or ammonium, preferably Na,
Y is an alkylene group linear or branched having 1 to 5 carbon atoms, preferably a methylene, or an ethylene group.

In the scope of the instant invention, the inventors have now found that polymers (P1) and (P2) as defined hereinabove define two distinct families of polymers which are efficient scale inhibitors with distinct spectroscopic absorption profiles.

More precisely, the family of the polymers (P1) have absorption maxima of less than 240 nm (usually between 215 and 240 nm) without any maxima over 240 nm, when the family of polymer (P2) has absorption maxima of more than 240 nm (commonly between 240 and 400 nm), with an absorption profile at less than 240 nm which is distinct from the absorption profile of the family of the polymers (P1).

In step (a) of the process, at least two inflow streams are injected into at least two production zones of an oil producing well linked to the oilfield, or into at least two different oil producing wells from which at least two outflow streams from the two zones or wells are combined, before recovering, with a scale inhibitor having detectable moieties being introduced into the oilfield(s) and/or into the fluid, wherein at least two different scale inhibitors are used, each dedicated to one of the two zones or wells, said different scale inhibitors having different detectable moieties. According to a specific embodiment, at least three inflow streams with at least three different scale inhibitors may are used, each dedicated to one of the zones or wells. For example, three, four or five inflow streams (preferably 3 or 4) with respectively three, four or five different scale inhibitors are used.

The polymers (P1) generally match the average general formula: (1)

$(X_2O_3P)_2CHYPO_2XZ1$                                       (1)

wherein X, Y have the significations given above and Z1 is the polymer chain resulting from the polymerisation of the ethylenically unsaturated carboxylic monomer; the ethylenically unsaturated sulphonic acid monomer or water soluble salts thereof; and the styrene monomer, in the presence of the adduct (A1). The presence of the styrene units induces an absorption of less than 240 nm. When the styrene monomer is substituted by one to three groups identical or different, those groups are preferably selected so that they do not confer to the polymer (P1) an absorption above 240 nm.

The polymers (P2) generally match the average general formula (2):

$(X_2O_3P)_2CHYPO_2XZ2$                                       (2)

wherein X, Y have the significations given above and Z2 is the polymer chain resulting from the polymerisation of the ethylenically unsaturated carboxylic monomer; the ethylenically unsaturated sulphonic acid monomer or water soluble salts thereof; and the vinyl heteroaromatic monomer, in the presence of the adduct (A2).

The presence of the vinyl heteroaromatic units induces at least an absorption maximum of more than 240 nm. When the vinyl heteroaromatic monomer is substituted by optionally functionalized hydrocarbon groups, these groups are selected so that they do not jeopardize this absorption maximum at more than 240 nm.

According to another aspect, the instant invention relates to each of the two families of polymers (P1) and (P2) useful in the method described above.

Thus, on the one hand, the invention relates to a first family, corresponding to the polymers of the (P1) type described above, which presents absorption maxima between 215 and 240 nm and having the average general formula (1):

$(X_2O_3P)_2CHYPO_2XZ1$                                       (1)

wherein X is H or an alkali metal, alkaline earth or ammonium, preferably Na, Y is an alkylene group linear or branched having 1 to 5 carbon atoms, preferably a methylene, or an ethylene group and Z1 is a polymer chain as obtained by polymerization of an ethylenically unsaturated carboxylic monomer with an ethylenically unsaturated sulphonic acid monomer or water soluble salts thereof and a styrenic monomer which can be substituted by one to three groups identical or different and selected to provide said absorption, in the presence of an hypophosphorous adduct of the formula (A1):

$$(X_2O_3P)_2CHYPO_2X_2 \tag{A1}$$

wherein X and Y have the significations given above.

The substituting groups of the styrene monomer are preferably chosen from H, $SO_3H$, $SO_3Na$, $NH_2$, COOH, $CH_2Cl$ and OH.

Examples of suitable styrenic monomers are gathered in the following table 1:

TABLE 1

| Monomer | Abbreviation | Structure |
|---|---|---|
| Amino styrene | AS | 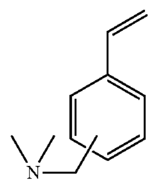 |
| N,N-dimethyl-vinylbenzylamine | DMVBA | 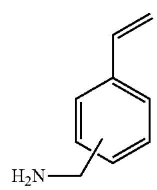 |
| Sodium styrene Sulphonate | NaSS | 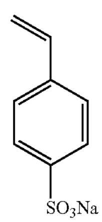 |
| Styrene Sulphonic acid | HSS | 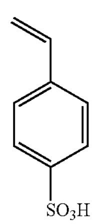 |
| 4-Vinyl benzylchloride | 4-VBC | 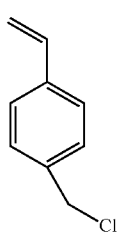 |

TABLE 1-continued

| Monomer | Abbreviation | Structure |
|---|---|---|
| Styrene carboxylic acid | SCA | 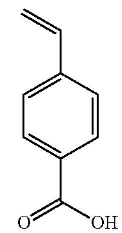 |

Examples of ethylenically unsaturated carboxylic monomers are acrylic acid, methacrylic acid, maleic acid, fumaric acid, itaconic acid, aconitic acid, mesaconic acid, citraconic acid, crotonic acid isocrotonic acid, angelic acid and tiglic acid. Examples of ethylenically unsaturated sulphonic acid monomer are vinyl sulphonic acid, styrene-p-sulphonic acid, and 2-acrylamido-2-methyl propane sulphonic acid, (meth)allyl sulfonic acid, (meth)allyloxybenzene sulfonic acid, sodium 1-allyloxy 2 hydroxy propyl sulfonic acid, A preferred ethylenically unsaturated sulphonic acid monomer are vinyl sulfonic acids and their water-soluble salts, particularly sodium, ammonium and potassium.

Preferred copolymers are copolymers of vinyl sulphonic acid with acrylic and/or maleic acid and/or vinyl phosphonic and/or vinylidene diphosphonic acid. Preferably such copolymers contain a major proportion of vinyl sulphonic acid groups.

The polymers of formula (1) can especially be prepared by the following preparation process comprising the steps of:

a) preparing the hypophosphorous adduct (A1) which is a tetrasodium alkylidene diphosphonate/hypophosphorous acid adduct prepared by addition of tetra-sodium alkylidene diphosphonate in an aqueous reaction medium at around 100° C., b) leaving under reflux the aqueous reaction medium and cooling it to room temperature, and c) recovering the solution of the hypophosphorous adduct formed, d) reacting said hypophosphorous adduct with an ethylenically unsaturated carboxylic monomer with an ethylenically unsaturated sulphonic acid monomer or water soluble salts thereof and a styrene monomer in the presence sodium persulphate, and e) recovering the polymer.

On the other hand, the invention relates to a second family of polymers, corresponding to the polymers of the (P2) type described above, which present at least one absorption maximum between 240 and 400 nm and have the average general formula (2):

$$(X_2O_3P)_2CHYPO_2XZ2 \tag{2}$$

wherein X is H or an alkali metal, alkaline earth or ammonium, preferably Na, Y is an alkylene group linear or branched having 1 to 5 carbon atoms, preferably a methylene, or an ethylene group and Z2 is a polymer chain as obtained by polymerization of an ethylenically unsaturated carboxylic monomer with an ethylenically unsaturated sulphonic acid monomer or water soluble salts thereof and an unsaturated vinyl heteroaromatic monomer comprising at least one heteroatom selected from N, P or O which can be substituted by by at least one hydrocarbon group having 1 to 6 carbon atoms and optionally containing functional groups such as sulphate, carboxylate, phosphonate and/or phosphinate, in the presence of an hypophosphorous adduct of the formula (A2):

$$(X_2O_3P)_2CHYPO_2X_2 \qquad (A^2)$$

wherein X and Y have the significations given above.

The ethylenically unsaturated carboxylic monomer and the ethylenically unsaturated sulphonic acid monomers which may be present in polymers of formula (2) may be selected among the same as those useful to prepare the polymers of formula (1).

Preferred unsaturated heterocycle monomers are: 2-vinyl pyridine (2VP), 4-vinyl pyridine (4VP), 1-(3-Sulfopropyl)-2-vinylpyridinium betaine (2-SPV), 1-(3-Sulfopropyl)-4-vinylpyridinium betaine (4-SPV), 1-vinyllmidazole (VI), 1-vinyl-1,2,4-triazole (VT), methyl vinyl triazole (MVT) More particularly, the preferred unsaturated heterocycle monomers are those of formula gathered in table 2 below:

TABLE 2

| Monomer | Abbreviation | Structure |
|---|---|---|
| 1-vinylimidazole | VI | 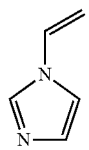 |
| 1-vinyl-1,2,4-triazole | VT | 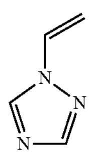 |
| Methyl Vinyl Thiazole | MVT | 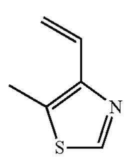 |
| 2-Vinyl pyridine | 2VP | 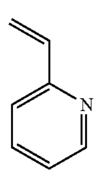 |
| 4-Vinyl pyridine | 4VP | 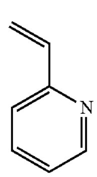 |
| 1-3-sulfopropyll-2-vinylpyridinium betaine | 2SPV | 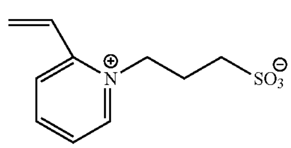 |
| 1-3-sulfopropyll-4-vinylpyridinium betaine | 4SPV | 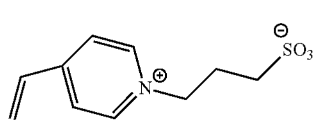 |

That second family of polymers of formula (2) can be prepared by means of the following preparation process comprising the steps of:

a) preparing the hypophosphorous adduct (A2) which is a tetrasodium alkylidene disphosphonate/hypophosphorous acid adduct prepared by addition of tetra-sodium alkylidene diphosphonate in an aqueous reaction medium at around 100° C., b) leaving under reflux the aqueous reaction medium and cooling it to room temperature, and c) recovering the solution of the hypophosphorous adduct formed, d) reacting said hypophosphorous adduct with an ethylenically unsaturated carboxylic monomer, with an ethylenically unsaturated sulphonic acid monomer or water soluble salts thereof and an unsaturated vinyl heteroaromatic monomer comprising at least one heteroatom selected from N, P or O which can be substituted by one or more alkyl groups having 1 to 6 carbon atoms in the presence of hydrosoluble initiators such as persulphate, bromates, peroxides, perborates, perchlorates, and azo initiators. Sodium persulphate is one of the preferred initiators. and e) recovering the polymer.

The polymers (P1) and (P2), notably the compounds of formulae (1) and (2) (also depicted herein as "scale inhibitors of family (1) and (2)") may be used alone or in admixture in squeeze treatment of oil wells. They are especially effective in preventing barium sulphate scale and calcium, for example a carbonate salt. For example in oil wells the hole is typically flushed out with aqueous surfactant to provide a water wettable surface and then impregnated with a solution of the inhibitor. In the case of calcium, the calcium salt may be formed in situ either by calcium in the formation, where the latter comprises limestone, or by prior, or subsequent, treatment of the hole with an aqueous calcium salt, for example carbonate, e.g. where the formation comprises sandstone.

Effective concentrations may typically range from 0.2 to 50 ppm, preferably 0.5 to 20 ppm depending on the nature of the aqueous system. For relatively soft water 1 to 20 ppm, most preferably 2 to 10 ppm, may give useful scale protection. Scale inhibitors of family (1) and (2) according to the invention may have to be used in combination with one another, and/or in conjunction with the other water treatment agents including: surfactants, such as anionic surfactants (e.g. C10-20 alkyl benzene sulphonates, C10-20 olefin sulphonates, C10-20 alkyl sulphates, C10-20 alkyl 1 to 25 mole ether sulphates, C10-20 parafinsulphonates, C10-20 soaps, C10-20 alkyl phenol sulphates, sulphosuccinates, sulphosuccinamates, lignin sulphonates, fatty ester sulphonates, C10-20 alkyl phenyl ether sulphates, C10-20 alkyl ethanolamide sulphates, C10-20 alpha sulphofatty acid salts, C10-20 acyl sarcosinates, isethionates, C10-20 acyl taurides, C10-20 alkyl hydrogen phosphates), non-ionic surfactants (e.g. ethoxylated and/or propoxylated C10-20 alcohols, ethoxylated and/or propoxylated C10-20 carboxylic acids, alkanolamides, amine oxides, and/or C10-20 acyl sorbitan and/or glyceryl ethoxylates) amphoteric surfactants (e.g. betaines, sulphobetaines, and/or quaternised imidazolines), and/or cationic surfactants (e.g. benzalkonium salts, C10-20 alkyl trimethyl ammonium salts, and/or C10-20 alkyl trimethyl or tris(hydroxymethyl) phosphonium slats); sequestrants, chelating agents, corrosion inhibitors and/or other threshold agents (e.g. sodium tripolyphosphate, sodium ethylenediamine tetraacetate, sodium nitrilo triacetate, tetra potassium pyrophosphate, acetodiphosphonic acid and its salts, ammonium trismethylene phosphonic acid and its salts, ethylenediamine tetrakis (methylene phosphonic) acid and its salts, diethylenetriamine pentakis (methylene phosphonic) acid and its salts); tolyltriazole and mixtures of nitrate, benzoate HHP and/or PTCB) biocides (e.g. tetrakis (hydroxymethyl) phosphonium salts, formaldehyde, glutaraldehyde); oxidising biocides and/or bleaches (e.g. chlorine, chlorine dioxide, hydrogen peroxide, sodium perborate); foam controlling agents such as silicone antifoams; oxygen scavengers such as hydrazines and/or hydroxylamines; pH controlling and/or buffering agents such as amines, borates, citrates and/or acetates; chromium salts; zinc salts; and/or other water treatment agents such as polymeric dispersants and coagulants including polymaleic, polyacrylic and polyvinylsulphonic acids and their salts, starches and/or carboxy methyl cellulose, and/or molybdates. The invention provides formulations comprising an effective amount of a product of the invention as aforesaid and any of the aforesaid known water treatment agents. Such formulations may, for example, contain from 5 to 95 by weight of a product of the invention and from 5 to 90% by weight of one or more of any of the aforesaid water treatment agents. Another aspect of the current invention relates to the use of those two families of polymers of formula (1) and (2) having different detectable moieties by means of their distinct absorption maxima so that they can be distinguished by analyzing by means of absorption analytical methods such as UV/VIS spectroscopy.

Preferably, the. substituting groups of the styrene monomer of the first family are preferably chosen from H, $SO_3H$, $SO_3Na$, $NH_2$, COOH, $CH_2Cl$, OH, —$CH_2OH$ and —$N(CH_3)2$.

The preferred analysis method is UV/VIS spectroscopy.
The following examples illustrate the invention.

EXAMPLE 1

Preparation of DPPE 480 g tetra-sodium vinylidene diphosphonate (37.4% aqueous solution, 0.47 moles) and 358 g hypophosphorus acid (16% aqueous solution, 0.47 moles) were charged to a reaction vessel and heated to 100° C.

22.3 g sodium persulphate (10% aqueous solution 0.0094 moles) were added via an addition funnel over 1 hour. The reaction mixture was left to reflux for further 2 hours and allowed to cool. The product contained no unreacted vinyl diphosphonate by $^{31}P$ NMR.

EXAMPLE 2

Preparation of DPPE Capped NaSS-stat-AA-stat-SVS Telomer

Into a 1 L jacketed reactor equipped with a reflux condenser and mechanical agitator was added Sodium Vinyl Sulphonate (127.7 g, 25% active), a solution of DPPE (70 g, 14.7% active) and a solution of Sodium Styrene Sulphonate (146.4 g, 10%). The reaction mixture was heated to reflux temperature (115° C. jacket temperature) with stirring. Once reflux temperature was attained, three feeds were added independently to the reactor. Feed 1 comprised acrylic acid (127.4 g, 80%) and was added to the reaction mixture over 120 minutes. Feed 2 was comprised of Sodium vinyl Sulphonate (383.2 g, 25% active) and Sodium Styrene Sulphonate (146.4 g, 10%) and was added in parallel over 120 minutes. The final feed was Sodium persulphate (84.2 g, 10%) and was added over 190 minutes. Upon completion of the persulphate feed, the reaction mixture was held at reflux temperature for a further 30 minutes wherapon it was cooled to room temperature and the solution discharged. Analysis by $^{31}P$ NMR revealed 75% of the DPPE adduct had been reacted to form polymeric species. Aqueous GPC gave a bimodal distribution with an Mn 3198, Mw 8947 g/mol. HPLC analysis demonstrated near quantitative conversion of Acrylic acid (<10 ppm) and Sodium Styrene Sulphonate (<10 ppm).

EXAMPLE 3

Preparation of DPPE Capped 2VP-stat-AA-stat-SVS Telomer

Into a 250 ml 3 necked round bottomed flask equipped with a reflux condenser and magnetic stirrer bar was added a solution of Sodium Vinyl Sulphonate (13.1 g, 25% active) and a solution of DPPE (5 g, 14.7% active). The reaction flask was heated in an oil bath set at 95° C. Once the targeted temperature was attained, three feeds were added independently to the flask. Feed 1 comprised acrylic acid (9.1 g, 80%) and 2-vinyl pyridine (1.1 g, 99.8%) and was added to the reaction mixture over 120 minutes. Feed 2 was comprised of Sodium vinyl Sulphonate (39.4, 25% active) and was added in parallel over 120 minutes. The final feed was Sodium Persulphate (6 g, 10%) and was added over 195 minutes. Upon completion of the Persulphate feed, the reaction mixture was held at temperature for a further 30 minutes whereupon it was cooled to room temperature and the solution discharged. Analysis by $^{31}P$ NMR revealed 60% of the DPPE adduct had been reacted to form polymeric species. Aqueous GPC (PEO calibration) gave a bimodal distribution with an Mn 3358, Mw 11580 g/mol. Multidetector GPC analysis (RI and UV @ 254 nm) confirmed homogenous incorporation of 2VP across the Molecular weight distribution. HPLC analysis demonstrated near quantitative conversion of Acrylic acid (<10 ppm) and 2-vinyl pyridine (<20 ppm).

EXAMPLE 4

Preparation of DPPE Capped 4VP-stat-AA-stat-SVS Telomer

Into a 250 ml 3 necked round bottomed flask equipped with a reflux condenser and magnetic stirrer bar was added a solution of Sodium Vinyl Sulphonate (13.1 g, 25% active) and a solution of DPPE (5 g, 14.7% active). The reaction flask was heated in an oil bath set at 95° C. Once the targeted temperature was attained, three feeds were added independently to the flask. Feed 1 comprised acrylic acid (9.1 g, 80%) and 4-vinyl pyridine (1.1 g, 99.8%) and was added to the reaction mixture over 120 minutes. Feed 2 was comprised of Sodium vinyl Sulphonate (39.4, 25% active) and was added in parallel over 120 minutes. The final feed was Sodium Persulphate (6 g, 10%) and was added over 195 minutes. Upon completion of the Persulphate feed, the reaction mixture was held at temperature for a further 30 minutes whereupon it was cooled to room temperature and the solution discharged. Analysis by $^{31}P$ NMR revealed 49.3% of the DPPE adduct had been reacted to form polymeric species. Aqueous GPC (PEO calibration) gave a bimodal distribution with an Mn 4300, Mw 8900 g/mol. Multidetector GPC analysis (RI and UV @ 254 nm) confirmed homogenous incorporation of 4VP across the Molecular weight distribution. HPLC analysis demonstrated near quantitative conversion of Acrylic acid (<10 ppm) and 4-vinyl pyridine (<20 ppm).

EXAMPLE 5

Preparation of DPPE Capped 2-SPV-stat-AA-stat-SVS Telomer

Into a 250 ml 3 necked round bottomed flask equipped with a reflux condenser and magnetic stirrer bar was added a solution of Sodium Vinyl Sulphonate (13.1 g, 25% active) and a solution of DPPE (5 g, 14.7% active). The reaction flask was heated in an oil bath set at 95° C. Once the targeted temperature was attained, three feeds were added independently to the flask. Feed 1 comprised acrylic acid (9.1 g, 80%), 1-(3-Sulfopropyl)-2-vinyl pyridinium betaine (2.32 g, 99%) and water (20.8 g) was added to the reaction mixture over 120 minutes. Feed 2 was comprised of Sodium Vinyl Sulphonate (39.4, 25% active) and was added in parallel over 120 minutes. The final feed was Sodium Persulphate (6 g, 10%) and was added over 195 minutes. Upon completion of the Persulphate feed, the reaction mixture was held at temperature for a further 30 minutes whereupon it was cooled to room temperature and the solution discharged. Analysis by $^{31}$P NMR revealed 44.9% of the DPPE adduct had been reacted to form polymeric species. Aqueous GPC (PEO calibration) gave a bimodal distribution with an Mn 11556, Mw 20580 g/mol. HPLC analysis demonstrated near quantitative conversion of Acrylic acid (<10 ppm) and 1-(3-Sulfopropyl)-2-vinyl pyridinium betaine (<20 ppm).

EXAMPLE 6

Preparation of DPPE Capped 4SPV-stat-AA-stat-SVS Telomer

Into a 250 ml 3 necked round bottomed flask equipped with a reflux condenser and magnetic stirrer bar was added a solution of Sodium Vinyl Sulphonate (13.1 g, 25% active) and a solution of DPPE (5 g, 14.7% active). The reaction flask was heated in an oil bath set at 95° C. Once the targeted temperature was attained, three feeds were added independently to the flask. Feed 1 comprised acrylic acid (9.1 g, 80%), 1-(3-Sulfopropyl)-4-vinyl pyridinium betaine (2.32 g, 99%) and water (20.8 g) was added to the reaction mixture over 120 minutes. Feed 2 was comprised of Sodium vinyl Sulphonate (39.4, 25% active) and was added in parallel over 120 minutes. The final feed was Sodium Persulphate (6 g, 10%) and was added over 195 minutes. Upon completion of the Persulphate feed, the reaction mixture was held at temperature for a further 30 minutes whereupon it was cooled to room temperature and the solution discharged. Analysis by $^{31}$P NMR revealed 47.2% of the DPPE adduct had been reacted to form polymeric species. Aqueous GPC (PEO calibration) gave a bimodal distribution with an Mn 5500, Mw 11300 g/mol. HPLC analysis demonstrated near quantitative conversion of Acrylic acid (<10 ppm) and 1-(3-Sulfopropyl)-4-vinyl pyridinium betaine (<20 ppm).

EXAMPLE 7

UV Absorbance Profile

UV absorber monomers synthesised in examples 2-6 have been detected using UV/VIS spectroscopy. For monomers, a 10 ppm (as active polymer) solution of each sample was prepared. For polymers, a 100 ppm (as active polymer) solution of each polymer was prepared. The pH of these solutions was adjusted at 5,5. The absorbance was then measured over the wavelength range of 200 nm to 400 nm in standard 1 cm path length cells using a Perkin Elmer UV/VIS spectrophotometer.

The absorbance maximum and the corresponding absorbance were determined for each sample.

The results are gathered in table 3 below.

TABLE 3

UV/VIS data Family 1

| Sample | Absorbance maximum (nm) | Corresponding Absorbance |
|---|---|---|
| NaSS monomer | 246 | 1.09 |
| Example 2 | 223 | 0.48 |

TABLE 4

UV/VIS data Family 2

| Sample | Absorbance maximum (nm) | Corresponding Absorbance |
|---|---|---|
| 2VP monomer | 278 | 0.92 |
| Example 3 | 264 | 0.25 |
| 4VP monomer | 246 | 1.05 |
| Example 4 | 258 | 0.18 |
| 2SPV monomer | 287 | 0.43 |
| Example 5 | 269 | 0.24 |
| 4SPV monomer | 271 | 0.63 |
| Example 6 | 257 | 0.13 |

Data from table 3 and 4 show a shift of maximum absorbance between UV-absorber monomers and polymers. This shift corresponds to a perfect incorporation of UV-absorber monomers during polymerisation.

EXAMPLE 8

Thermal Stability of UV Profiles

Solutions of polymers from example 2 to 6 were made up to the desired concentration (5% active polymer) in synthetic sea water. The pH was adjusted to 5.5. 60 mls of each solution was poured into a Teflon liner (internal volume of 100 mls) of a stainless steel bomb. The individual solutions were then degassed for approximately 30 minutes. The Teflon liners were then sealed and placed into the stainless steel bombs which were placed in an oven at 212° F. for 1 week. Following this, the bombs were allowed to cool.

The UV absorption profiles were determined for each aged solution after dilution at 100 ppm active polymer and compared to the one obtained on un-aged solution at the same concentration. The UV absorption profile before and after aging are exactly the same.

EXAMPLE 9

Barium Sulfate Scale Inhibition

The polymers prepared in examples 2-6 were tested for their ability to inhibit barium sulphate scale formation. The test method for measuring inhibition of barium sulphate consisted of measuring the level of soluble barium after mixing of two incompatible salt solutions in a bottle, then observing the change in the mixture without agitation for a given time, and measuring the soluble barium by a spectroscopic method (ICP-AES). The experiments include a control test without inhibitor and tests in the presence of inhibitors.

This evaluation was carried out at 95° C. and pH 5.5 after mixing two brines, one of which has the composition of the formation water of the Forties Field in the North Sea (contains barium) and the other has the seawater composition containing sulfate. The inhibitor was placed in the seawater. The inhibitor concentration was 15 ppm (of active ingredient) relative to the final mixture. The pH of the seawater solution containing inhibitor was brought to about 5.5 with a sodium acetate/acetic acid buffer solution.

The brine compositions (Forties water and seawater) were the following:

| Ion | mg/L | Salt | Salt (g/L) |
|---|---|---|---|
| Forties Water | | | |
| $Na^+$ | 31275 | NaCl | 79.50 |
| $Ca^+$ | 2000 | $CaCl_2$, $2H_2O$ | 7.34 |
| $Mg^{2+}$ | 739 | $MgCl_2$, $6H_2O$ | 6.18 |
| $K^+$ | 654 | KCl | 1.25 |
| $Ba^2$ | 269 | $BaCl_2$, $2H_2O$ | 0.48 |
| $Sr^{2+}$ | 87.6 | $SrCl_2$, $6H_2O$ | 2.35 |
| Seawater | | | |
| $Na^+$ | 10890 | NaCl | 24.40 |
| $Ca^{2+}$ | 428 | $CaCl_2$, $2H_2O$ | 1.57 |
| $Mg^{2+}$ | 1368 | $MgCl_2$, $6H_2O$ | 11.44 |
| $K^+$ | 460 | KCl | 0.88 |
| $SO_4^{2-}$ | 2690 | $Na_2SO_4$ | 3.97 |

100 ml of each of these liquids was placed in polyethylene bottles. Once the temperature of the brines has settled to 95° C. in an oven, the contents of the "Forties water" bottle were poured into the bottle containing the barium. The mixture was shaken manually then replaced in the oven at 95° C. for 2 hours. For each test series, two control tests were run:

Min blank: this is a test without inhibitor and the barium ion content will be minimal (maximum precipitation of $BaSO_4$);

Max blank: this is a test without sulfate and without inhibitor; the seawater is replaced by purified water and the barium ion content will be maximal as there is no precipitation.

After two hours of testing, the bottles were removed from the oven and a 5 ml sample is taken then diluted in 5 ml of a "soaking" solution whose composition is: 5000 ppm KCl/1000 ppm PVA (polyvinyl sodium sulfonate) adjusted to pH 8-8.5 (with 0.01 N NaOH). The barium from these samples is assayed (ICP-AES) and the inhibition effectiveness deduced, expressed in the formula below:

$$\% \text{ efficiency} = \frac{[Ba^{2+}] - [Ba^{2+}]_{min}}{[Ba^{2+}]_{max} - [Ba^{2+}]_{min}} * 100$$

where $[Ba^{2+}]_{max} = Ba^{2+}$ concentration in max blank $[Ba^{2+}]_{min} = Ba^{2+}$ concentration in min blank The results are shown in the following table 5.

TABLE 5

| Inhibitor | % $BaSO_4$ inhibition effectiveness (15 ppm) |
|---|---|
| Example 2 | 37 |
| Example 3 | 42 |
| Example 4 | 45 |
| Example 5 | 42 |
| Example 6 | 48 |

This test was also conducted on thermally aged polymers obtained in example 8, i.e. thermal aging Sea Water at 122° F. during 1 week. The level of performance measured on aged polymers was the same as the one measured on fresh polymers and presented in table 4.

EXAMPLE 10

Adsorption on Clay Under Static Conditions

The additives according to the invention were evaluated for their ability to adsorb on clay.

For this purpose, a solution of known concentration of inhibitor in synthetic brine was brought into contact for 20 hours, at 85° C., with a known quantity of solid. The solid suspension was then centrifuged and filtered, then analyzed in terms of dissolved organic carbon. The adsorbed amount was measured using the following protocol:

For each solution of additive diluted in seawater at the concentration in question, the organic carbon concentration ($COT_{SM}$ in ppm) and a response coefficient K (additive concentration in solution/organic carbon concentration in solution) were determined.

The organic carbon concentration ($COT_{filtrate}$ in ppm) in the supernatant solution after adsorption was determined.

The adsorbed quantity (QA) was then calculated using the following formula:

$$QA = \frac{(COT_{SM} - COT_{Filtrate}) \times K \times V_{SM}}{1000 \times M_{Solid} \times S_{BET}}$$

where:

SM = volume of solution in $cm^3$ $M_{Solid}$ = mass of solid in grams $S_{BET}$ = specific surface of solid The clay used was ground kaolinite. Its specific surface measured by the BET method with nitrogen was 12 $m^2/g$. For each product, solutions of 1.0 mg/l active ingredient were prepared in a brine which composition is presented in the table below.

| Salt | Concentration (g/l) |
|---|---|
| NaCl | 2.4 |
| $MgCl_2$, $6H_2O$ | 5.7 |
| $CaCl_2$, $2H_2O$ | 1.5 |

For each test, 15 ml of solution and 2.0 g of kaolinite were used, i.e. a liquid:solid ratio of 7.5.

The results are shown in the following Table 6 below.

TABLE 6

| Inhibitor | Quantity Adsorbed (mg additive/m² clay |
|---|---|
| Example 2 | 0.28 |
| Example 3 | 0.31 |
| Example 4 | 0.33 |
| Example 5 | 0.39 |
| Example 6 | 0.31 |

The invention claimed is:

1. A method for imparting scale inhibition in an oilfield, the method comprising the steps of:
   a) injecting at least two inflow streams of a fluid into at least two production zones of an oil producing well that is linked to the oilfield, or into at least two different oil producing wells that are linked to the oilfield, wherein scale inhibitor having detectable moieties is introduced into the oilfield and/or into the fluid, so as to be present in the two zones or wells, wherein two different scale inhibitors are introduced, one for each of the two zones or wells, said different scale inhibitors having different detectable moieties, such that these different scale inhibitors have distinct absorption maxima that can be determined by an absorption analytical method;
   b) displacing oil from the oil producing well;
   c) recovering an outflow stream of fluid comprising the oil;
   wherein at least two outflow streams, one from each of the two zones or one from each of the two wells, are combined before said recovering; and
   d) measuring the amounts of the different scale inhibitors present in the recovered stream of fluid, or in a fluid derived from the recovered stream of fluid, by an absorption analytical method;
   and wherein one of the two scale inhibitors is a polymer (P1) as obtained by polymerization of:
   an ethylenically unsaturated carboxylic monomer;
   an ethylenically unsaturated sulphonic acid monomer or water soluble salts thereof;
   a styrene monomer, optionally substituted by one to three groups;
   in the presence of an hypophosphorous adduct of the formula (A1):

$(X_2O_3P)_2CHYPO_2X_2$ (A1)

wherein:
   X is H or an alkali metal, alkaline earth or ammonium,
   Y is an alkylene group, which may be linear or branched, having from 1 to 5 carbon atoms;
   and wherein the other one of the two scale inhibitors is a polymer (P2) as obtained by polymerization of:
   an ethylenically unsaturated carboxylic monomer;
   an ethylenically unsaturated sulphonic acid monomer or water soluble salts thereof;
   a vinyl heteroaromatic monomer comprising at least one heteroatom selected from N, P and O, which can be substituted by at least one hydrocarbon group having 1 to 6 carbon atoms, and which optionally contains functional groups;
   in the presence of an hypophosphorous adduct of the formula (A1):

$(X_2O_3P)_2CHYPO_2X_2$ (A1)

wherein:
   X is H or an alkali metal, alkaline earth or ammonium,
   Y is an alkylene group, which may be linear or branched, having from 1 to 5 carbon atoms,
   whereby the hypophoshorous adducts of the formula (A1) are identical or distinct.

2. The method of claim 1, wherein if in step (d) the amount of one of the two scale inhibitors is below a predetermined value, the method further comprises the step of:
   e) addressing a scale formation problem in the zone or well that is associated with said scale inhibitor.

3. The method of claim 1, wherein the absorption analytical method is UV/VIS spectroscopy.

4. The method of claim 1, wherein in formula (A1) Y is a methylene or an ethylene group.

5. The method of claim 1, wherein in formula (A1) X is sodium (Na).

6. The method of claim 1, wherein the vinyl heteroaromatic monomer contains sulphate, carboxylate, phosphonate and/or phosphinate functional groups.

7. A polymer having an absorption maximum between 215 and 240 nm and having an average general formula (1):

$(X_2O_3P)_2CHYPO_2XZ1$ (1)

wherein
X is H or an alkali metal, alkaline earth or ammonium,
Y is an alkylene group, which may be linear or branched, having from 1 to 5 carbon atoms, and
Z1 is a polymer chain obtained by polymerization of an ethylenically unsaturated carboxylic monomer with an ethylenically unsaturated sulphonic acid monomer or water soluble salts thereof and a styrene monomer, which can be substituted by one to three groups that may be identical or different, and which are selected to provide said absorption maximum, in the presence of an hypophosphorous adduct of the formula (A1):

$(X_2O_3P)_2CHYPO_2X_2$ (A1)

wherein X and Y have the same meaning as in formula (1).

8. A polymer as defined in claim 7, wherein the substituent groups of the styrene monomer are chosen from H, SO₃H, SO₃Na, NH₂, Me₂N, COOH, CH₂Cl, CH₂OH and OH.

9. A polymer as defined in claim 7, wherein the ethylenically unsaturated carboxylic monomer is selected from the group consisting of: acrylic acid, methacrylic acid, maleic acid, fumaric acid, itaconic acid, aconitic acid, mesaconic acid, citraconic acid, crotonic acid isocrotonic acid, angelic acid and tiglic acid.

10. A polymer as defined in claim 7, wherein the ethylenically unsaturated sulphonic acid monomer is selected from the group consisting of: vinyl sulphonic acid, 2-acrylamido-2-methyl propane sulphonic acid, allyl sulphonic acid, and methallyl sulphonic acid.

11. A polymer as defined in claim 7, wherein the polymer is selected from the group consisting of: copolymers of vinyl sulphonic acid with acrylic and/or maleic acid and/or vinyl phosphonic and/or vinylidene diphosphonic acid.

12. A polymer having an absorption maximum between 240 and 400 nm and having an average general formula (2):

$(X_2O_3P)_2CHYPO_2XZ2$ (2)

wherein
X is H or an alkali metal, alkaline earth or ammonium,
Y is an alkylene group, which may be linear or branched, having from 1 to 5 carbon atoms, and Z2 is a polymer chain obtained by polymerization of an ethylenically unsaturated carboxylic monomer with an ethylenically unsaturated sulphonic acid monomer or water soluble salts thereof and a vinyl heteroaromatic monomer, which can be substituted by one to three groups that may be identical or different, and selected to provide said absorption maximum, in the presence of an hypophosphorous adduct of the formula (A2):

$$(X_2O_3P)_2CHYPO_2X_2 \qquad (A2)$$

wherein X and Y have the same meaning as in formula (2).

13. A polymer as defined in claim 12, wherein the ethylenically unsaturated carboxylic monomer is selected from the group consisting of: acrylic acid, methacrylic acid, maleic acid, fumaric acid, itaconic acid, aconitic acid, mesaconic acid, citraconic acid, crotonic acid, isocrotonic acid, angelic acid and tiglic acid.

14. A polymer as defined in claim 12, wherein the ethylenically unsaturated sulphonic acid monomer is selected from the group consisting of: vinyl sulphonic acid, 2-acrylamido-2-methyl propane sulphonic acid, allyl sulphonic acid, and methallyl sulphonic acid.

15. A polymer as defined in claim 12, wherein the polymer is selected from the group consisting of: copolymers of vinyl sulphonic acid with acrylic and/or maleic acid and/or vinyl phosphonic and/or vinylidene diphosphonic acid.

* * * * *